United States Patent
Juergens et al.

(10) Patent No.: US 12,421,553 B2
(45) Date of Patent: Sep. 23, 2025

(54) METHOD OF DIAGNOSING ASTHMA SUBTYPES

(71) Applicant: Rheinische Friedrich-Wilhelms-Universitaet Bonn, Bonn (DE)

(72) Inventors: Uwe Juergens, Niederkassel (DE); Bernd Merzenich, Niederkassel (DE); Gudrun Sigrid Ulrich-Merzenich, Niederkassel (DE)

(73) Assignee: Rheinische Friedrich-Wilhems-Universitaet Bonn, Bonn (DE)

( * ) Notice: Subject to any disclaimer, the term of this patent is extended or adjusted under 35 U.S.C. 154(b) by 1152 days.

(21) Appl. No.: 17/262,239

(22) PCT Filed: Jul. 25, 2019

(86) PCT No.: PCT/EP2019/070071
§ 371 (c)(1),
(2) Date: Jan. 22, 2021

(87) PCT Pub. No.: WO2020/021026
PCT Pub. Date: Jan. 30, 2020

(65) Prior Publication Data
US 2021/0301345 A1    Sep. 30, 2021

(30) Foreign Application Priority Data
Jul. 25, 2018 (EP) .................... 18185472

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

2016/0186259 A1* 6/2016 Ofir .................... G01N 33/6803 506/7

FOREIGN PATENT DOCUMENTS

| EP | 2931920 A1 | 10/2015 |
|---|---|---|
| WO | 2009124090 A1 | 10/2009 |
| WO | 2014089636 A1 | 6/2014 |

OTHER PUBLICATIONS

Pukelsheim et al., "Cytokine Profiles in Asthma Families Depend on Age and Phenotype", PLoS One, 2010, pp. 1-11, vol. 5, No. 12.
Meyer et al., "Differential serum protein markers and the clinical severity of asthma", Journal of Asthma and Allergy, 2014, 3 pages, vol. 7.
Barnes, "The cytokine network in chronic obstructive pulmonary disease", The Journal of Clinical Investigation, 2008, pp. 3546-3556, vol. 118, No. 11.
Robinson et al., "Revisiting Type 2-high and Type 2-low airway inflammation in asthma: current knowledge and therapeutic implications", Clinical & Experimental Allergy, 2017, pp. 161-175, vol. 47.
Extended European search report from parallel European Patent Application 18 185 472.0 dated Dec. 4, 2018, 10 pages (for reference purposes only).
International search report from parallel PCT Patent Application PCT/EP2019/070071 dated Nov. 25, 2019, 11 pages (for reference purposes only).

* cited by examiner

Primary Examiner — Aaron A Priest
(74) Attorney, Agent, or Firm — Rimon Law

(57) ABSTRACT

Methods of diagnosing an asthma subtype in a patient using a combinatory asthma endotyping assay are described. In various embodiments, a kit and a marker panel may be used in these methods.

2 Claims, 2 Drawing Sheets

METHOD OF DIAGNOSING ASTHMA SUBTYPES

CROSS-REFERENCE TO RELATED APPLICATION

The present application is a national stage entry according to 35 U.S.C. § 371 of PCT application No.: PCT/EP2019/070071 filed on Jul. 25, 2019; which claims priority to European Patent Application Serial No.: 18185472.0 filed on Jul. 25, 2018; all of which are incorporated herein by reference in their entirety and for all purposes.

TECHNICAL FIELD

The present invention relates to methods of diagnosing an asthma subtype in a patient using a combinatory asthma endotyping assay. Furthermore, the invention relates to a kit and a marker panel for use in these method.

BACKGROUND

According to the Global Asthma Report 2014 of the Global Asthma Network (GAN) Steering group, 330 million people worldwide currently suffer from asthma. The World Health Organisation (WHO) and the Global Initiative for Asthma estimate that about 230 until 300 million people are affected. Hence, asthma belongs to the most frequent diseases and mortality is estimated to reach about 250,000 annually. According to data from Robert Koch-Institut asthma prevalence, namely the percentage of persons who are likely to develop asthma, has increased between 2003 and 2009: for women from 6.0% to 10.1%, for men from 5.2% to 8.3%. Long-term prognosis however assumes that the prevalence of the disease will remain stable.

In Europe, prevalence of asthma is reported to be in the range of from 5% to 10%. Despite prescribed medication, a minority of patients show only partially controlled asthma or even uncontrolled asthma. This so-called "severe asthma" is economically important, since this patient group consumes a major part of the financial resources. To date, decisions regarding therapy are mostly made based on practical knowledge or analogous cases only due to the heterogeneity of the disease.

Immunotherapy is one viable treatment option for asthma. Due to the more frequent use of immunotherapy in recent years, for example in pulmonology, rheumatology or oncology, the healthcare sector has experienced significantly increased treatment costs. Immunotherapy is typically combined with the treatment by other drugs and within the authorized indication. As a result, up to two third of the patients receive a therapy with little effect or even no effect at all and sometimes severe side effects.

Moreover, not all patients respond to immunotherapy authorized for their pathology. For example, only a third of the patients with melanoma respond to the antibody treatment of PD-1 or CTL-A4 with Nivolumab or Ipilimumab. This means that 6 to 7 out of 10 patients receive medication which is expensive and has side effects without having the desired clinical effect.

Since 2005, Omalizumab (IgE-Ak) can be prescribed in cases of severe allergic asthma. About two thirds of the patients who receive this antibody show the desired response. Due to the heterogeneity of the disease, extensive research is ongoing and alternative antibodies are or will soon be available, for example Interleukin-4Rx inhibitors (anti-IL4Ra antibodies), Dupilumab (antibody against IL-4 and IL-13), Lebrikizumab or Tralokizumab (anti-IL-13 antibodies) and Mepolizumab, Reslizumab or Benralizumab (anti-IL-5 antibodies or receptor inhibitors) or IL-33 antibodies, as well as enzymes, such as GATA3-DNAzyme. The authorization of alternative antibody therapies are expected for the coming years, but it is to be expected that the costs for these new therapy options will be significantly higher compared to Omalizumab treatment.

Due to the growing number of antibody therapies available and the costs involved, there is need, from an ethical and an economic point of view, that a precise identification of the best suitable antibody therapy for the indication "severe asthma" can be obtained and an optimized response of the patients to the prescribed antibody therapy can be ensured by means of an appropriate differentiation with specific diagnostic or prediction means in the sense of "precision medicine" or "personalized medicine".

SUMMARY

In a first aspect, a method of identifying an asthma subtype in a patient may include a) determining, in a sample from a patient, the gene expression level of at least six genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more selected from the group selected from IL-8, IL-10, IL-12, IL-27, TNF-α, CD94, IL-3, IL-9, IL-31, IL-35, CCL11 and TGF-β (also called hereinafter genes of interest), evaluating the data of a), preferably by means of a software, wherein the software is configured to generate a gene expression profile specific to the patient, and determining the asthma subtype of the patient by comparing the gene expression profile of the patient obtained in step b) with a reference gene expression profile.

A reference gene expression profile may be the gene expression profile of a healthy individual. Alternatively or additionally, the step of determining the asthma subtype of the patient by comparing the gene expression profile of the patient obtained with a reference gene expression profile may be based on the data measured in the sample of the patient and a database which comprises a plurality of gene expression profiles and a plurality of asthma subtypes, wherein a specific asthma subtype is assigned to each gene expression profile of the plurality of gene expression profiles. The assignment in the database may be established experimentally, for example by means of laboratory experiments and practice experience with asthma patients. The database may be based and updated on experience values from a plurality of asthma patients and publicly accessible data.

In some embodiments of the method described herein, the software used for the evaluation of the data to generate a gene expression profile specific to the patient is based on combinatory algorithms and determines the asthma type of the patient from the measured gene expression levels of the at least six genes of interest, and, optionally, from predetermined clinical and chemical parameters of asthma subtypes existing in asthma patients. In the latter case, the specific asthma subtype of a patient is then determined from the combination of the "basic diagnosis" based on clinical and chemical parameters and the "endotypical profile" based on gene expression levels.

This basic diagnosis based on clinical and chemical parameters typically involves the determination of the levels of IgE, eosinophils, neutrophils and/or FeNO in a blood sample of the patient, preferably at least IgE and eosinophil levels, are determined. If IgE values and eosinophil levels are given herein, those are indicated in IU/ml (IgE) and cells/μl (eosinophil), respectively, if not indicated otherwise.

In various embodiments of the method described herein, the asthma subtype is a severe asthma type, preferably an asthma subtype selected from the group consisting of, but not limited to, a severe allergic asthma, a severe non-allergic asthma, eosinophilic allergic asthma, non-eosinophilic allergic asthma, neutrophilic asthma, non-allergic asthma, Th-1-cell characterized asthma, Th-2-cell characterized asthma, Th1 low/Th2 high asthma and Th-17-cell characterized asthma.

In certain embodiments of the method described herein, the determination of the gene expression level of the at least six genes of interest is performed using a combinatory asthma endotyping assay kit comprising the detection reagents for measuring the gene expression level of the at least six genes of interest.

In some embodiments of the method described herein, the sample is a biological sample.

In various embodiments of the method described herein, the sample is a body fluid, cell or tissue sample.

In certain embodiments of the method described herein, the body fluid is selected from the group consisting of blood, serum, plasma and saliva, preferably blood. Independent of the sample type, gene expression analysis of the marker genes, as described herein, covers the expression in all cells contained in the sample. In blood samples, this means that the gene expression in the white blood cells, namely lymphocytes, contained in the sample is determined. In various embodiments, gene expression analysis is thus performed on full blood samples, thus assaying gene expression of the total population of lymphocytes contained in said sample.

In various embodiments of the method described herein, the patient is a human.

In certain embodiments of the method described herein, the gene expression level is measured by assaying for protein level or the mRNA or cDNA level.

In some embodiments of the method described herein, the protein level is determined by an immunoassay, ELISA, by the application of microbeads covered with fluorescent marker conjugated antibodies directed towards analytes followed by flow cytometry methods to determine the concentration of the soluble analytes, by mass spectrometry, by chromatography, by Western Blot or by gel electrophoresis.

In various embodiments of the method described herein, the mRNA level or cDNA level is measured by PCR method, preferably RT-PCR, or microarray chip or by sequencing.

In a second aspect, a kit for use in the method may include a combinatory asthma endotyping kit comprising detection reagents for measuring the gene expression level of at least six genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more selected from the group selected from IL-8, IL-10, IL-12, IL-27, TNF-α, CD94, IL-3, IL-9, IL-31, IL-35, CCL11 and TGF-β or fragments thereof, optionally further including an instruction manual for measuring the gene expression level of the genes comprised in the combinatory asthma endotyping kit and, optionally, a software, wherein the software is configured to evaluate data measured and determine the asthma subtype of the patient.

In some embodiments of the kit described herein, the gene expression is measured by assaying for mRNA levels or cDNA levels. In such embodiments, the kit may comprise primers for the detection and quantification of expression levels of the at least six genes of interest.

In certain embodiments of the kit described herein, the panel is suitable for use in a PCR method, preferably RT-PCR either in a suitable microarray plate or as a microarray chip or as digital PCR.

In a third aspect, the kit may be used in the method.

In a fourth aspect, a combinatory asthma endotyping panel may include detection reagents for measuring the gene expression level of at least six genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more selected from the group selected from IL-8, IL-10, IL-12, IL-27, TNF-α, CD94, IL-3, IL-9, IL-31, IL-35, CCL11 and TGF-β or fragments thereof, for use in a method.

Additional advantages and aspects will become apparent from the following detailed description and the appended claims.

BRIEF DESCRIPTION OF THE DRAWINGS

FIG. 1 shows a schematic drawing of the layout of a 96-well PCR microplate for one patient, wherein the gene expression level of up to 32 genes can be determined, with three replicates.

FIG. 2 shows a schematic drawing of the layout of a 384-well PCR microplate for one to three patients, wherein the gene expression level of up to 32 genes can be determined, with four replicates.

FIG. 3 shows a schematic drawing of the layout of a dedicated PCR microplate compatible with the 384-well format for one patient, wherein the gene expression level of up to 32 genes can be determined, with four replicates.

FIG. 4 shows a schematic drawing of a layout of a lab-on-chip device for one patient, wherein the gene expression level of up to 32 genes can be determined, with four replicates.

DETAILED DESCRIPTION

Unless otherwise defined, all terms of art, notations and other scientific terminologies used herein are intended to have the meanings commonly understood by those of skill in the art. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted.

Throughout this specification and claims, the word "comprise," or variations such as "comprises" or "comprising," will be understood to imply the inclusion of a stated feature or group of features but not the exclusion of any other feature or group of features.

The term "asthma", as used herein, refers to a comprehensive disease name collectively referred to as various diseases characterized by inflammation of airways leading to organs, bronchi, bronchioles and alveoli. More specifically, asthma is a condition in which the bronchus in the lung is very sensitive.

The term "asthma subtype" as used herein encompasses "asthma endotypes" or "asthma phenotypes". The term "asthma phenotype", as used herein, describes "observable characteristics" like clinical, physiological, morphological, inflammatory and biochemical characteristics as well as the response to different treatments with no direct relationship to a disease process. The term "asthma endotype", as used herein, is defined by a distinct functional or pathological (e.g. cellular/inflammatory response) mechanism. The asthma endotype may encompass several phenotypes just as certain phenotypes may be present in more than one endotype. The asthma subtype may be, but is not limited to, severe allergic asthma, severe allergic asthma, a severe non-allergic asthma, eosinophilic allergic asthma, non-eosinophilic allergic asthma, neutrophilic asthma, non-allergic asthma, Th-1-cell characterized asthma, Th-2-cell characterized asthma, Th1 low/Th2 high asthma and Th-17-cell characterized asthma.

The term "diagnosis" as used herein means to identify the presence or characteristic of a pathological condition. A diagnosis is used to confirm whether a patient is afflicted by asthma or not, and, if positively diagnosed, to distinguish the subtype of asthma a patient is suffering from.

The term "elevated expression level" or "elevated levels" or "increased level", as used exchangeably herein, refers to an increased expression of a mRNA or cDNA or a protein in a patient relative to a control, the control being an individual or individuals who are not suffering from asthma.

The term "decreased expression level" or "decreased level" refers to a decreased expression of a mRNA or cDNA or a protein in a patient relative to a control, the control being an individual or individuals who are not suffering from asthma.

As used herein, the term "mRNA or cDNA level measurement" is used to determine the presence and expression level of mRNA or cDNA, respectively, in asthmatic diagnostic genes in a biological sample to diagnose asthma. RT-PCR, Competitive RT-PCR, Real-time RT-PCR, digital PCR, RNase protection (RPA) assay, Northern blotting, DNA chip, sequencing and the like are methods that may be used to determine the mRNA level or cDNA level.

As used herein, the term "protein level measurement" is a process for determining the presence and expression level of an asthma diagnostic marker protein in a biological sample for asthma diagnosis. The amount of the protein can be confirmed using an antibody that specifically binds to the marker protein.

A relationship was discovered between the expression level of specific genes and an asthma subtype in a patient and uses a combinatory evaluation of a specific gene expression profile obtained from the patient that allows the evaluation/determination of the individual immunological reactivity and, as a result, a detailed diagnosis and therapy decision in the sense of personalized medicine. Based on the combinatory methodology, targeted drug development (as well as combination preparations or combination therapies) becomes possible.

The method is a dedicated genomic diagnosis means, for example at the transcriptome level, for immunologic endotyping of severe asthma conditions in the clinical routine. As mentioned in the introductory part, the method represents a specific diagnosis means that allows an allocation of a precise antibody therapy choice for the indication "severe asthma" in the sense of "precision medicine" or "personalized medicine". By the method, an optimized response of the patients to the prescribed antibody therapy can be ensured, avoiding treatments of patients suffering from asthma with non-effective antibody therapeutics and thus reducing the burden of the diagnosis for the patients suffering from asthma. Furthermore, the method uses tissue and/or body fluid samples, e.g., a blood sample or sputum, and thus provides for a novel method for the diagnosis of an asthma subtype. As the method does not require expensive equipment, the expenditure of cost and time for asthma subtyping can be reduced. Furthermore, the new method can be carried out by most common screening laboratories and therefore does not require the patient to travel to specific screening centers. Another advantage of the method is that, besides its simple and cost-effective production and use, the method uses a combinatory asthma endotyping panel which is compatible with usual and common laboratory devices, for example PCR laboratory devices, so that no product specific infrastructure is necessary for performing the method.

The method is based on the combinational measurement and evaluation of the gene expression level, for example at the mRNA, cDNA or protein level, of a pre-determined number of markers, in particular cytokines or receptors specific for asthma subtypes. The gene expression level is measured, for example by means of RNA or protein determination, for example from venous blood from patient suffering from asthma. The qualitative and quantitative evaluation for endotyping the asthma condition is subsequently performed by means of a dedicated software.

In a first aspect, a method of diagnosing an asthma subtype in a patient by using a combinatory asthma endotyping assay. The method comprises the steps of a) determining, in a sample from the patient, the gene expression level of at least six, at least seven, at least eight, at least nine, at least ten, at least 11, at least 12, at least 13, at least 14, at least 15, at least 16, at least 17 or all 18 genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more, two or more, 3 or more, 4 or more, 5 or more, 6 or more, 7 or more, 8 or more, 9 or more, 10 or more, 11 or more or all 12 of the genes selected from the group selected from IL-8, IL-10, IL-12, IL-27, TNF-α, CD94, IL-3, IL-9, IL-31, IL-35, CCL11 and TGF-β or fragments thereof; b) evaluating the data of step a), preferably by means of a software, wherein the software is configured to generate a gene expression profile specific to the patient; and c) determining the asthma subtype of the patient by comparing the gene expression profile specific to the patient obtained in step b) with a reference gene expression profile.

TABLE 1

List of the genes of interest and their respective ID number

| No. | Gene | Gene ID |
|---|---|---|
| 1 | 18s RNA (reference) | ribosomal/human |
| 2 | GAPDH (reference) | 2597 |
| 3 | IL-1β | 3553 |
| 4 | IL-6 | 3569 |
| 5 | IL-8 | 3576 |
| 6 | IL-10 | 3586 |
| 7 | IL-12 | 3592, 3593 |
| 8 | IL-27 | 246778 |
| 9 | IFN-γ | 3458 |
| 10 | TNF-α | 7124 |

TABLE 1-continued

List of the genes of interest and their respective ID number

| No. | Gene | Gene ID |
|---|---|---|
| 11 | CD94 | 3024 |
| 12 | IL-2 | 3558 |
| 13 | IL-3 | 3562 |
| 14 | IL-4 | 3565 |
| 15 | IL-5 | 3567 |
| 16 | IL-9 | 3578 |
| 17 | IL-13 | 3596 |
| 18 | IL-21 | 59067 |
| 19 | IL-25 | 64806 |
| 20 | IL-31 | 386653 |
| 21 | IL-33 | 90865 |
| 22 | IL-35/IL-12A* | 3592 |
| 23 | IL-37 | 27178 |
| 24 | TSLP | 85480 |
| 25 | GATA-3 | 2625 |
| 26 | CCR3 | 1232 |
| 27 | CCL11 | 6356 |
| 28 | IL-17A | 3605 |
| 29 | IL-22 | 50616 |
| 30 | IL-23 | 51561 |
| 31 | GM-CSF | 1437 |
| 32 | TGF-β | 7040 |

The gene IDs refer to those obtained from the NCBI Gene Data Base (www.ncbi.nlm.nih.gov/gene/). If no indicated otherwise, the version of the gene is that of Jul. 23, 2018 or the most recent version preceding Jul. 23, 2018.

In a second aspect, an assay kit for use in the method may include a combinatory asthma endotyping kit comprising detection reagents for measuring the gene expression level of at least six, at least seven, at least eight, at least nine, at least ten, at least 11, at least 12, at least 13, at least 14, at least 15, at least 16, at least 17 or all 18 genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more, two or more, 3 or more, 4 or more, 5 or more, 6 or more, 7 or more, 8 or more, 9 or more, 10 or more, 11 or more or all 12 of the genes selected from the group selected from IL-8, IL-10, IL-12, IL-27, TNF-α, CD94, IL-3, IL-9, IL-31, IL-35, CCL11 and TGF-β or fragments thereof; optionally further including an instruction manual for measuring the gene expression level of the genes comprised in the combinatory asthma endotyping kit and, optionally, a software, wherein the software is configured to evaluate data measured and determine the asthma subtype of the patient.

In a third aspect, the kit may be used in the method.

In a fourth aspect, a combinatory asthma endotyping panel may include detection reagents for measuring the gene expression level of at least six, at least seven, at least eight, at least nine, at least ten, at least 11, at least 12, at least 13, at least 14, at least 15, at least 16, at least 17 or all 18 genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more, two or more, 3 or more, 4 or more, 5 or more, 6 or more, 7 or more, 8 or more, 9 or more, 10 or more, 11 or more or all 12 of the genes selected from the group selected from IL-8, IL-10, IL-12, IL-27, TNF-α, CD94, IL-3, IL-9, IL-31, IL-35, CCL11 and TGF-β or fragments thereof, for use in a method.

When compared to a reference gene expression level, typically of a healthy individual, i.e. an individual not afflicted by asthma, the measured gene expression level may be evaluated as being decreased ("−"), unchanged ("o"), slightly increased ("+"), moderately increased ("++") and strongly increased ("+++").

An increased gene expression level means that the expression is increased relative to a normal state, i.e. a healthy control, i.e. the level in a healthy individual, namely in an individual not afflicted by asthma. In various embodiments, a gene expression level is considered increased, if the gene expression level of the gene of interest (also called "marker gene") is greater than a predetermined threshold, for example, when the gene expression level of the gene of interest is greater than 1.8 fold relative to a healthy control gene expression level (or greater than 1.2 fold, for example, in the case of the gene of interest IL-35 and, optionally, greater than 1.8 fold for all other genes of interest). The concrete values of the respective threshold for each marker gene are listed in the table below. As already defined above, such an increased gene expression level can be further rated to be slightly, moderately or strongly increased.

Similarly, a decreased gene expression level means that the gene expression level is decreased relative to a normal state. In various embodiments, a gene expression level of a gene of interest is considered decreased, if the level is equal to or below the level of a healthy control gene expression level (ratio determined level/control level≤1.0).

If not indicated otherwise, the respective threshold values are determined using quantitative real time PCR (qRT-PCR) with appropriate primers and an appropriate control, such as the GADPH expression. Primers for a given gene of interest are commercially available and can be designed by those skilled in the art by routine techniques and methods. The threshold values for the genes of interest (also called "marker genes") listed in the following table are based on $2^{\wedge}\Delta CT$ of the qRT-PCR, e.g. the factor of the increase or decrease, respectively, of the gene expression of the respective patient in relation to the average value of the control collective of healthy individuals.

TABLE 2

Gene expression values (x-fold increase relative to control)

| No. | Gene | − | o | + | ++ | +++ |
|---|---|---|---|---|---|---|
| 1 | 18s | — | — | — | — | — |
| 2 | GAPDH | — | — | — | — | — |
| 3 | IL-1β | ≤1.0 | >1.0 ≤ 1.8 | >1.8 ≤ 10 | >10 ≤ 100 | >100 |
| 4 | IL-6 | ≤1.0 | >1.0 ≤ 1.8 | >1.8 ≤ 5 | >5 ≤ 15 | >15 |
| 5 | IL-8 | ≤1.0 | >1.0 ≤ 1.8 | >1.8 ≤ 3 | >3 ≤ 10 | >10 |
| 6 | IL-10 | ≤1.0 | >1.0 ≤ 1.8 | >1.8 ≤ 4 | >4 ≤ 10 | >10 |
| 7 | IL-12 | ≤1.0 | >1.0 ≤ 1.8 | >1.8 ≤ 4 | >4 ≤ 10 | >10 |
| 8 | IL-27 | ≤1.0 | >1.0 ≤ 1.8 | >1.8 ≤ 5 | >5 ≤ 10 | >10 |
| 9 | IFN-γ | ≤1.0 | >1.0 ≤ 1.8 | >1.8 ≤ 5 | >5 ≤ 10 | >10 |
| 10 | TNF-α | ≤1.0 | >1.0 ≤ 1.8 | >1.8 ≤ 10 | >10 ≤ 30 | >30 |
| 11 | CD94 | ≤1.0 | >1.0 ≤ 1.8 | >1.8 ≤ 4 | >4 ≤ 10 | >10 |

TABLE 2-continued

Gene expression values (x-fold increase relative to control)

| No. | Gene | − | o | + | ++ | +++ |
|---|---|---|---|---|---|---|
| 12 | IL-2 | ≤1.0 | >1.0 ≤ 1.8 | >1.8 ≤ 3 | >3 ≤ 10 | >10 |
| 13 | IL-3 | ≤1.0 | >1.0 ≤ 1.8 | >1.8 ≤ 20 | >20 ≤ 30 | >30 |
| 14 | IL-4 | ≤1.0 | >1.0 ≤ 1.8 | >1.8 ≤ 15 | >15 ≤ 80 | >80 |
| 15 | IL-5 | ≤1.0 | >1.0 ≤ 1.8 | >1.8 ≤ 20 | >20 ≤ 1000 | >1000 |
| 16 | IL-9 | ≤1.0 | >1.0 ≤ 1.8 | >1.8 ≤ 4 | >4 ≤ 10 | >10 |
| 17 | IL-13 | ≤1.0 | >1.0 ≤ 1.8 | >1.8 ≤ 4 | >4 ≤ 15 | >15 |
| 18 | IL-21 | ≤1.0 | >1.0 ≤ 1.8 | >1.8 ≤ 3 | >3 ≤ 10 | >10 |
| 19 | IL-25 | ≤1.0 | >1.0 ≤ 1.8 | >1.8 ≤ 3 | >3 ≤ 10 | >10 |
| 20 | IL-31 | ≤1.0 | >1.0 ≤ 1.8 | >1.8 ≤ 20 | >20 ≤ 100 | >100 |
| 21 | IL-33 | ≤1.0 | >1.0 ≤ 1.8 | >1.8 ≤ 10 | >10 ≤ 50 | >50 |
| 22 | IL-35 | ≤1.0 | >1.0 ≤ 1.2 | >1.2 ≤ 1.5 | >1.5 ≤ 2.0 | >2.0 |
| 23 | IL-37 | ≤1.0 | >1.0 ≤ 1.8 | >1.8 ≤ 4 | >4 ≤ 10 | >10 |
| 24 | TSLP | ≤1.0 | >1.0 ≤ 1.8 | >1.8 ≤ 4 | >4 ≤ 10 | >10 |
| 25 | GATA-3 | ≤1.0 | >1.0 ≤ 1.8 | >1.8 ≤ 100 | >10 ≤ 50 | >50 |
| 26 | CCR3 | ≤1.0 | >1.0 ≤ 1.8 | >1.8 ≤ 10 | >100 ≤ 150 | >150 |
| 27 | CCL11 | ≤1.0 | >1.0 ≤ 1.8 | >1.8 ≤ 10 | >10 ≤ 100 | >100 |
| 28 | IL-17A | ≤1.0 | >1.0 ≤ 1.8 | >1.8 ≤ 10 | >10 ≤ 1000 | >1000 |
| 29 | IL-22 | ≤1.0 | >1.0 ≤ 1.8 | >1.8 ≤ 3 | >3 ≤ 10 | >10 |
| 30 | IL-23 | ≤1.0 | >1.0 ≤ 1.8 | >1.8 ≤ 20 | >20 ≤ 1000 | >1000 |
| 31 | GM-CSF | ≤1.0 | >1.0 ≤ 1.8 | >1.8 ≤ 5 | >5 ≤ 20 | >20 |
| 32 | TGF-β | ≤1.0 | >1.0 ≤ 1.8 | >1.8 ≤ 5 | >5 ≤ 20 | >20 |

A weighed evaluation of the classification "−", "o", "+", "++", and "+++" resulting from the values of a patient specific gene expression profile is compared with "ideal subtype profiles" to determine the patient subtype profile according to the greatest amount of matches obtained with an "ideal subtype profile". In this weighed evaluation of the gene expression values, a gene expression level is considered "indicative" for a given subtype, if the gene expression level is classified as being "ideal" or "preferred" in the respective ideal subtype profiles shown in Tables 4 to 8 below. In other words, a gene expression level is considered to be "indicative" for a subtype, if it is within the "preferred" or "ideal" expression levels as given in the below tables for the respective subtype. In more concrete embodiments, a gene expression level is considered to be "indicative" for a subtype, if it is within the "ideal" expression levels as given in Tables 4 to 8. If a gene expression level is deemed "inconclusive", as used in the below tables, this means that said marker value does not allow any conclusions regarding the subtype. "Not permitted", as used in the tables, means that said gene expression value is counter-indicative for said subtype. In various embodiments, if a core marker, as defined below, is found to be "not permitted", the respective subtype may be ruled out based on this markers gene expression level alone. For each subtype, a set of 8 core markers has been defined, the expression of which has particular relevance for assigning a subtype. In various embodiments, the expression of at least 6 of those core markers are determined to allow diagnosing a given subtype for which those markers are defined as core markers. The core markers of the 5 subtypes disclosed herein, are those shown in Table 3 below.

TABLE 3

List of „core markers" for all subtypes SP1 to SP5

| Gene | Core marker Subtype 1 | Core marker Subtype 2 | Core marker Subtype 3 | Core marker Subtype 4 | Core marker Subtype 5 |
|---|---|---|---|---|---|
| IL-1β |  | ● |  |  |  |
| IL-6 | ● | ● | ● | ● |  |
| IL-8 |  |  |  |  |  |
| IL-10 |  |  |  |  |  |
| IL-12 |  |  |  |  |  |
| IL-27 |  |  |  |  |  |
| IFN-γ |  | ● |  | ● |  |
| TNF-α |  |  |  |  |  |
| CD94 |  |  |  |  |  |
| IL-2 | ● | ● | ● |  |  |
| IL-3 |  |  |  |  |  |
| IL-4 | ● | ● | ● | ● | ● |
| IL-5 |  |  |  | ● | ● |
| IL-9 |  |  |  |  |  |
| IL-13 |  |  |  | ● |  |
| IL-21 | ● | ● | ● |  |  |
| IL-25 | ● |  |  |  |  |
| IL-31 |  |  |  |  |  |
| IL-33 | ● | ● | ● | ● | ● |
| IL-35 |  |  |  |  |  |
| IL-37 |  |  |  |  | ● |
| TSLP | ● |  | ● | ● |  |
| GATA-3 |  |  |  | ● |  |
| CCR3 |  |  |  | ● | ● |
| CCL11 |  |  |  |  |  |
| IL-17A | ● | ● | ● | ● | ● |
| IL-22 |  |  |  |  | ● |
| IL-23 |  |  |  |  | ● |
| GM-CSF |  |  |  |  | ● |
| TGF-β |  |  |  |  |  |

The following ideal subtype profiles are disclosed herein:

SP1=subtype of a patient suffering from eosinophilic asthma, for whom a treatment with anti-IgE antibody without steroid intake is appropriate. The ideal subtype profile thereof with respect to the gene expression profile of the marker genes disclosed herein is as shown in Table 4 below (also see Example 3, Table 9) with the symbols used as described above and the values provided in Table 2. "Preferred", as used in this table, means that said values are not ideal but still within the range for said subtype, i.e. indicative for said subtype.

TABLE 4

Ideal SP1 subtype

| No. | Gene | − | o | + | ++ | +++ |
|---|---|---|---|---|---|---|
| 1 | 18s | — | — | — | — | — |
| 2 | GAPDH | — | — | — | — | — |
| 3 | IL-1β | inconclusive | inconclusive | ideal | inconclusive | not permitted |
| 4 | IL-6 | not permitted | not permitted | preferred | preferred | ideal |
| 5 | IL-8 | preferred | preferred | preferred | ideal | preferred |
| 6 | IL-10 | preferred | preferred | preferred | preferred | ideal |
| 7 | IL-12 | preferred | preferred | preferred | ideal | preferred |
| 8 | IL-27 | inconclusive | inconclusive | inconclusive | inconclusive | ideal |
| 9 | IFN-γ | not permitted | preferred | preferred | ideal | preferred |
| 10 | TNF-α | not permitted | not permitted | preferred | preferred | ideal |
| 11 | CD94 | preferred | preferred | preferred | preferred | ideal |
| 12 | IL-2 | not permitted | not permitted | preferred | preferred | ideal |
| 1 | IL-3 | preferred | preferred | ideal | preferred | not permitted |
| 0 | IL-4 | not permitted | not permitted | preferred | preferred | ideal |
| 15 | IL-5 | inconclusive | inconclusive | preferred | inconclusive | inconclusive |
| 16 | IL-9 | inconclusive | preferred | inconclusive | inconclusive | inconclusive |
| 17 | IL-13 | inconclusive | inconclusive | inconclusive | inconclusive | inconclusive |
| 18 | IL-21 | ideal | preferred | preferred | inconclusive | not permitted |
| 19 | IL-25 | not permitted | not permitted | preferred | preferred | ideal |
| 20 | IL-31 | inconclusive | preferred | inconclusive | inconclusive | inconclusive |
| 21 | IL-33 | not permitted | not permitted | preferred | preferred | ideal |
| 22 | IL-35 | ideal | preferred | not permitted | not permitted | not permitted |
| 23 | IL-37 | inconclusive | ideal | preferred | preferred | not permitted |
| 24 | TSLP | not permitted | not permitted | preferred | preferred | ideal |
| 25 | GATA-3 | not permitted | not permitted | preferred | ideal | not permitted |
| 26 | CCR3 | not permitted | not permitted | preferred | preferred | ideal |
| 27 | CCL11 | not permitted | not permitted | preferred | preferred | ideal |
| 28 | IL-17A | inconclusive | inconclusive | ideal | preferred | not permitted |
| 29 | IL-22 | inconclusive | ideal | preferred | inconclusive | not permitted |
| 30 | IL-23 | inconclusive | ideal | preferred | inconclusive | not permitted |
| 31 | GM-CSF | inconclusive | ideal | preferred | inconclusive | not permitted |
| 32 | TGF-β | inconclusive | ideal | preferred | inconclusive | not permitted |

The above marker levels may be combined with basic diagnostic parameters, as described above. Of particular importance for this subtype are IgE and eosinophil (without steroids) levels. An IgE level of equal to or more than 300 IU/mL and eosinophil levels of >300 and ≤700 cells/μl are indicative for this subtype. These values can be determined by routine measures known to those skilled in the art.

For example, this means that for diagnosing SP1 subtype, IL-33 levels >50 (="+++") would be ideal, e.g. highly indicative for SP1, whereas a decrease to <1.8 ("o" or "−") would be counter-indicative.

For every subtype, thus an "ideal profile" of the increase/decrease of the gene expression values (=factor values) for the respective asthma subtype is determined.

The major and novel part of this combinatory method to diagnosing an asthma subtype is the determination of the "expression profile" of a patient and its comparison with the defined expression profiles for the asthma subtypes. This (major) part of the method is herein named "endotypical profiling".

SP2=subtype of a patient suffering from eosinophilic asthma, for whom a treatment with anti-IgE antibody with steroid intake is appropriate. The ideal subtype profile thereof with respect to the gene expression profile of the marker genes disclosed herein is as shown in Table 5 below (also see Example 5 and Table 13) with the symbols used as described above and the values provided in Table 2. The terms used have the same meaning as in Table 4.

TABLE 5

Ideal SP2 subtype

| No. | Gene | − | o | + | ++ | +++ |
|---|---|---|---|---|---|---|
| 1 | 18s | — | — | — | — | — |
| 2 | GAPDH | — | — | — | — | — |
| 3 | IL-1β | inconclusive | preferred | ideal | preferred | inconclusive |
| 4 | IL-6 | inconclusive | preferred | ideal | preferred | inconclusive |
| 5 | IL-8 | inconclusive | inconclusive | inconclusive | inconclusive | inconclusive |
| 6 | IL-10 | ideal | preferred | preferred | not permitted | not permitted |
| 7 | IL-12 | preferred | ideal | preferred | not permitted | not permitted |
| 8 | IL-27 | inconclusive | inconclusive | inconclusive | inconclusive | inconclusive |
| 9 | IFN-γ | ideal | preferred | preferred | inconclusive | not permitted |
| 10 | TNF-α | ideal | preferred | preferred | inconclusive | not permitted |
| 11 | CD94 | ideal | preferred | preferred | inconclusive | not permitted |
| 12 | IL-2 | inconclusive | preferred | ideal | preferred | inconclusive |
| 1 | IL-3 | preferred | ideal | preferred | inconclusive | not permitted |
| 0 | IL-4 | not permitted | preferred | ideal | preferred | inconclusive |
| 15 | IL-5 | inconclusive | inconclusive | preferred | inconclusive | inconclusive |
| 16 | IL-9 | inconclusive | inconclusive | inconclusive | inconclusive | inconclusive |

TABLE 5-continued

| | | Ideal SP2 subtype | | | | |
|---|---|---|---|---|---|---|
| No. | Gene | − | o | + | ++ | +++ |
| 17 | IL-13 | inconclusive | inconclusive | inconclusive | inconclusive | inconclusive |
| 18 | IL-21 | ideal | preferred | preferred | not permitted | not permitted |
| 19 | IL-25 | inconclusive | preferred | ideal | preferred | inconclusive |
| 20 | IL-31 | inconclusive | preferred | inconclusive | inconclusive | inconclusive |
| 21 | IL-33 | inconclusive | preferred | ideal | inclonclusive | inconclusive |
| 22 | IL-35 | ideal | preferred | not permitted | not permitted | not permitted |
| 23 | IL-37 | not permitted | ideal | preferred | preferred | inconclusive |
| 24 | TSLP | inconclusive | preferred | ideal | inconclusive | inconclusive |
| 25 | GATA-3 | not permitted | ideal | preferred | not permitted | not permitted |
| 26 | CCR3 | inconclusive | preferred | ideal | preferred | inconclusive |
| 27 | CCL11 | inconclusive | preferred | ideal | preferred | inconclusive |
| 28 | IL-17A | preferred | ideal | preferred | not permitted | not permitted |
| 29 | IL-22 | preferred | ideal | preferred | not permitted | not permitted |
| 30 | IL-23 | preferred | ideal | preferred | not permitted | not permitted |
| 31 | GM-CSF | preferred | ideal | preferred | not permitted | not permitted |
| 32 | TGF-β | preferred | ideal | preferred | not permitted | not permitted |

The above marker levels may be combined with basic diagnostic parameters, as described above. Of particular importance for this subtype are IgE and eosinophil (with steroids) levels. A IgE level of equal to or more than 300 IU/mL and eosinophil levels of >200 and ≤500 cells/µl are indicative for this subtype.

SP3=subtype of a patient suffering from neutrophilic asthma, for whom a treatment with anti-IgE antibody without steroid intake is appropriate. The ideal subtype profile thereof with respect to the gene expression profile of the marker genes disclosed herein is as shown in Table 6 below (also see Example 7, Table 16) with the symbols used as described above and the values provided in Table 2. The terms used have the same meaning as in Table 4.

TABLE 6

| | | Ideal SP3 subtype | | | | |
|---|---|---|---|---|---|---|
| No. | Gene | − = −1 | o = 1 | + = 2 | ++ = 3 | +++ = 4 |
| 1 | 18s | — | — | — | — | — |
| 2 | GAPDH | — | — | — | — | — |
| 3 | IL-1β | inconclusive | inconclusive | ideal | inconclusive | not permitted |
| 4 | IL-6 | not permitted | inconclusive | inconclusive | preferred | ideal |
| 5 | IL-8 | inconclusive | inconclusive | preferred | preferred | ideal |
| 6 | IL-10 | inconclusive | inconclusive | inconclusive | preferred | ideal |
| 7 | IL-12 | inconclusive | inconclusive | preferred | ideal | preferred |
| 8 | IL-27 | inconclusive | inconclusive | inconclusive | inconclusive | inconclusive |
| 9 | IFN-γ | inconclusive | inconclusive | preferred | ideal | preferred |
| 10 | TNF-α | inconclusive | inconclusive | preferred | ideal | preferred |
| 11 | CD94 | inconclusive | inconclusive | preferred | preferred | ideal |
| 12 | IL-2 | not permitted | not permitted | preferred | preferred | ideal |
| 1 | IL-3 | preferred | ideal | preferred | inconclusive | not permitted |
| 0 | IL-4 | not permitted | not permitted | preferred | preferred | ideal |
| 15 | IL-5 | ideal | preferred | preferred | inconclusive | not permitted |
| 16 | IL-9 | inconclusive | inconclusive | inconclusive | inconclusive | inconclusive |
| 17 | IL-13 | not permitted | not permitted | preferred | inconclusive | inconclusive |
| 18 | IL-21 | inconclusive | inconclusive | ideal | preferred | preferred |
| 19 | IL-25 | not permitted | not permitted | ideal | preferred | not permitted |
| 20 | IL-31 | inconclusive | inconclusive | inconclusive | inconclusive | inconclusive |
| 21 | IL-33 | not permitted | not permitted | preferred | preferred | ideal |
| 22 | IL-35 | ideal | preferred | not permitted | not permitted | not permitted |
| 23 | IL-37 | not permitted | ideal | preferred | preferred | inconclusive |
| 24 | TSLP | not permitted | not permitted | preferred | ideal | preferred |
| 25 | GATA-3 | inconclusive | ideal | preferred | not permitted | not permitted |
| 26 | CCR3 | inconclusive | ideal | preferred | inconclusive | inconclusive |
| 27 | CCL11 | inconclusive | ideal | preferred | inconclusive | inconclusive |
| 28 | IL-17A | inconclusive | inconclusive | preferred | ideal | not permitted |
| 29 | IL-22 | inconclusive | ideal | preferred | preferred | not permitted |
| 30 | IL-23 | inconclusive | ideal | preferred | preferred | not permitted |
| 31 | GM-CSF | inconclusive | ideal | preferred | preferred | not permitted |
| 32 | TGF-β | inconclusive | ideal | preferred | preferred | not permitted |

The above marker levels may be combined with basic diagnostic parameters, as described above. Of particular importance for this subtype are IgE, eosinophil and neutrophil levels. An IgE level of higher than or equal to 300 IU/mL, eosinophil (without steroids) levels of ≤300 and neutrophil (without steroids) levels of ≥67% (only if eosinophils are lower than or equal to 300) are indicative for this subtype.

SP4=subtype of a patient suffering from eosinophilic asthma, for whom a treatment with anti-IL-5 antibody without steroid intake is appropriate. The ideal subtype profile thereof with respect to the gene expression profile of the marker genes disclosed herein is as shown in Table 7 below (also see Example 9 and Table 19) with the symbols used as described above and the values provided in Table 2. The terms used have the same meaning as in Table 4.

TABLE 7

Ideal SP4 subtype

| No. | Gene | - = -1 | o = 1 | + = 2 | ++ = 3 | +++ = 4 |
|---|---|---|---|---|---|---|
| 1 | 18s | — | — | — | — | — |
| 2 | GAPDH | — | — | — | — | — |
| 3 | IL-1β | not permitted | preferred | preferred | ideal | preferred |
| 4 | IL-6 | inconclusive | preferred | ideal | preferred | inconclusive |
| 5 | IL-8 | ideal | preferred | inconclusive | inn | inconclusive |
| 6 | IL-10 | ideal | preferred | inconclusive | inconclusive | inconclusive |
| 7 | IL-12 | inconclusive | preferred | ideal | inconclusive | inconclusive |
| 8 | IL-27 | inconclusive | inconclusive | inconclusive | inconclusive | inconclusive |
| 9 | IFN-γ | inconclusive | inconclusive | preferred | ideal | inconclusive |
| 10 | TNF-α | inconclusive | preferred | ideal | preferred | inconclusive |
| 11 | CD94 | inconclusive | preferred | ideal | preferred | inconclusive |
| 12 | IL-2 | inconclusive | preferred | ideal | preferred | inconclusive |
| 1 | IL-3 | not permitted | ideal | preferred | preferred | inconclusive |
| 0 | IL-4 | not permitted | inconclusive | preferred | ideal | preferred |
| 15 | IL-5 | not permitted | not permitted | preferred | preferred | ideal |
| 16 | IL-9 | not permitted | inconclusive | preferred | ideal | preferred |
| 17 | IL-13 | not permitted | inconclusive | preferred | preferred | ideal |
| 18 | IL-21 | preferred | ideal | preferred | inconclusive | not permitted |
| 19 | IL-25 | inconclusive | inconclusive | ideal | preferred | preferred |
| 20 | IL-31 | inconclusive | inconclusive | inconclusive | inonclusive | inconclusive |
| 21 | IL-33 | inconclusive | inconclusive | preferred | ideal | preferred |
| 22 | IL-35 | not permitted | ideal | preferred | inconclusive | inconclusive |
| 23 | IL-37 | not permitted | ideal | preferred | preferred | inconclusive |
| 24 | TSLP | inconclusive | inconclusive | ideal | preferred | not permitted |
| 25 | GATA-3 | not permitted | inconclusive | preferred | preferred | ideal |
| 26 | CCR3 | not permitted | inconclusive | preferred | preferred | ideal |
| 27 | CCL11 | not permitted | inconclusive | preferred | preferred | ideal |
| 28 | IL-17A | ideal | preferred | preferred | inconclusive | not permitted |
| 29 | IL-22 | ideal | preferred | preferred | inconclusive | not permitted |
| 30 | IL-23 | inconclusive | ideal | preferred | preferred | not permitted |
| 31 | GM-CSF | inconclusive | ideal | preferred | inconclusive | not permitted |
| 32 | TGF-β | inconclusive | ideal | preferred | inconclusive | not permitted |

The above marker levels may be combined with basic diagnostic parameters, as described above. Of particular importance for this subtype are IgE and eosinophil levels. A IgE level of equal to or higher than 300 IU/mL and eosinophil (without steroids) levels of higher than 700 cells/μl are indicative for this subtype.

SP5=subtype of a patient suffering from eosinophilic asthma, for whom a treatment with anti-IL-17 antibody without steroid intake is appropriate. The ideal subtype profile thereof with respect to the gene expression profile of the marker genes disclosed herein is as shown in Table 8 below (also see Example 12) with the symbols used as described above and the values provided in Table 2. The terms used have the same meaning as in Table 4.

TABLE 8

Ideal SP5 subtype

| No. | Gene | - = -1 | o = 1 | + = 2 | ++ = 3 | +++ = 4 |
|---|---|---|---|---|---|---|
| 1 | 18s | — | — | — | — | — |
| 2 | GAPDH | — | — | — | — | — |
| 3 | IL-1β | preferred | ideal | preferred | inconclusive | not permitted |
| 4 | IL-6 | inconclusive | inconclusive | ideal | preferred | preferred |
| 5 | IL-8 | ideal | preferre | preferred | not permitted | not permitted |
| 6 | IL-10 | preferred | ideal | preferred | inconclusive | not permitted |

TABLE 8-continued

Ideal SP5 subtype

| No. | Gene | − = −1 | o = 1 | + = 2 | ++ = 3 | +++ = 4 |
|---|---|---|---|---|---|---|
| 7 | IL-12 | inconclusive | inconclusive | ideal | preferred | preferred |
| 8 | IL-27 | not | ideal | preferred | inconclusive | inconclusive |
| 9 | IFN-γ | preferred | ideal | preferred | inconclusive | not permitted |
| 10 | TNF-α | ideal | preferred | preferred | inconclusive | not permitted |
| 11 | CD94 | preferred | ideal | preferred | inconclusive | inconclusive |
| 12 | IL-2 | preferred | ideal | preferred | preferred | not permitted |
| 1 | IL-3 | not permitted | inconclusive | ideal | preferred | inconclusive |
| 0 | IL-4 | not permitted | not permitted | ideal | preferred | preferred |
| 15 | IL-5 | not permitted | inconclusive | ideal | preferred | preferred |
| 16 | IL-9 | inconclusive | preferred | ideal | preferred | not permitted |
| 17 | IL-13 | inconclusive | ideal | preferred | inconclusive | not permitted |
| 18 | IL-21 | ideal | preferred | inconclusive | inconclusive | not permitted |
| 19 | IL-25 | not permitted | inconclusive | ideal | preferred | preferred |
| 20 | IL-31 | inconclusive | ideal | preferred | preferred | not permitted |
| 21 | IL-33 | ideal | preferred | inconclusive | not permitted | not permitted |
| 22 | IL-35 | not permitted | inconclusive | ideal | preferred | preferred |
| 23 | IL-37 | inconclusive | inconclusive | preferred | ideal | preferred |
| 24 | TSLP | not permitted | ideal | preferred | inconclusive | inconclusive |
| 25 | GATA-3 | inconclusive | preferred | ideal | not permitted | not permitted |
| 26 | CCR3 | inconclusive | ideal | preferred | inconclusive | not permitted |
| 27 | CCL11 | inconclusive | preferred | ideal | preferred | inconclusive |
| 28 | IL-17A | not permitted | not permitted | inconclusive | preferred | ideal |
| 29 | IL-22 | not permitted | not permitted | inconclusive | preferred | ideal |
| 30 | IL-23 | not permitted | not permitted | inconclusive | preferred | ideal |
| 31 | GM-CSF | not permitted | not permitted | inconclusive | preferred | ideal |
| 32 | TGF-β | not permitted | not permitted | inconclusive | preferred | ideal |

The above marker levels may be combined with basic diagnostic parameters, as described above. Of particular importance for this subtype are IgE and eosinophil levels. A IgE level of equal to or more than 300 IU/mL and eosinophil (without steroids) levels of >300 and ≤700 cells/μl are indicative for this subtype.

In the case of additional existing infections, the same subtype profile as without steroid is generally, but not automatically, relevant.

Additional subtype profiles can be defined, once new antibodies for therapy are tested and/or authorized.

In the method of diagnosing, determining the gene expression levels of at least six genes (also called genes of interest or core markers) selected from the group consisting of determining, in a sample from a patient, the gene expression level of at least six genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more selected from the group selected from IL-8, IL-10, IL-12, IL-27, TNF-α, CD94, IL-3, IL-9, IL-31, IL-35, CCL11 and TGF-β or fragments thereof may include determining the gene expression levels of 6, 7, 8, 9, 10, 11, 12, 13, 14, 15, 16, 17, 18, 19, 20, 21, 22, 23, 24, 25, 26, 27, 28, 29 or 30 genes, preferably determining the gene expression levels of 6, 7, 8, 9, 10, 11, 12, 13 or 14 genes. In various embodiments, the gene expression levels of at least 6, 7, 8, 9, 10, 11, 12, 13, 14, 15, 16, 17 or 18 of the genes of the first group are determined. In various additional embodiments, these gene expression levels of the first group may be combined with at least 1, 2, 3, 4, 5, 6, 7, 8, 9, 10, 11 or all 12 marker genes of the second group. Determining the gene expression level of a higher number of genes may increase the accuracy of the method. In addition to the above, the expression levels of further genes that correlate with asthmatic conditions may be measured additionally.

In one embodiment, the at least 6 genes of interest are preferably selected from the core marker genes as shown in Table 2. This means For SP1:
IL-6, IL-2, IL-4, IL-21, IL-25, IL-33, TSLP and IL-17A
For SP2:
IL-1β, IL-6, IL-2, IL-4, IL-21, IL-33, IFN-γ and IL-17A,
For SP3:
IL-6, IL-2, IL-4, IL-21, IL-33, TSLP, CCR3 and IL-17A,
For SP4:
IFN-γ, IL-4, IL-5, IL-13, IL-33, GATA-3, CCR3 and IL-17A,
For SP5:
IL-4, IL-5, IL-33, IL-37, IL-17A, IL-22, IL-23 and GM-CSF.

In various embodiments, at least 7 or all 8 of the indicated genes are selected for determining the respective subtype. In order to allow diagnosis of all different subtypes in one assay, the above listed core markers may be combined such that more than 6 and up to all 18 of these genes are assayed for their expression levels.

These core markers for the respective subtype, may be combined with additional markers that also have relevance for the diagnosis of the respective subtype. These are, in various embodiments, For SP1:
IFN-γ, IL-3, IL-5, IL-9, IL-22, IL-23, GM-CSF and TGF-β;
For SP2:
TSLP, IL-3, IL-5, IL-22, IL-23, GM-CSF and TGF-β;
For SP3:
IFN-γ, IL-5, IL-22, IL-23, GM-CSF and TGF-β;
For SP4:
IL-10, IL-12, IL-2, IL-3, IL-5, IL-21, IL-25, CCL11, IL-22, IL-23, GM-CSF and TGF-β; or
For SP5:
IL-6, IFN-γ, IL-21, IL-25 and TGF-β.

These marker combinations may be combined with the basic diagnostic parameters, as defined above, in particular the IgE levels and eosinophil/neutrophil levels.

In various embodiments,
(a) the patient is diagnosed with asthma subtype 1, if
(a1) the IgE level is equal to or higher than 300 IU/mL and the eosinophil level without steroids is in the range of >300 and ≤700 cells/µl; and
(a2) the gene expression of any 6 or more, 7 or more or all 8 of the genes selected from IL-6, IL-2, IL-4, IL-21, IL-25, IL-33, TSLP and IL-17A is indicative for subtype 1; and, optionally,
(a3) the gene expression of at least 1 of the genes selected from IFN-γ, IL-3, IL-5, IL-9, IL-22, IL-23, GM-CSF and TGF-β is indicative for subtype 1;
(b) the patient is diagnosed with asthma subtype 2, if
(b1) the IgE level is equal to or higher than 300 IU/mL and the eosinophil level with steroids is in the range of >200 and ≤500 cells/µl; and
(b2) the gene expression of any 6 or more, 7 or more or all 8 of the genes selected from IL-1β, IL-6, IL-2, IL-4, IL-21, IL-33, IFN-γ and IL-17A is indicative for subtype 2; and, optionally,
(b3) the gene expression of at least 1 of the genes selected from TSLP, IL-3, IL-5, IL-22, IL-23, GM-CSF and TGF-β is indicative for subtype 2;
(c) the patient diagnosed with asthma subtype 3, if
(c1) the IgE is equal to or higher than 300 IU/mL, the eosinophil level without steroids is ≤300 cells/µl and the neutrophil level without steroids is ≥67% (only if eosinophils are lower than or equal to 300); and
(c2) the gene expression of any 6 or more, 7 or more or all 8 of the genes selected from IL-6, IL-2, IL-4, IL-21, IL-33, TSLP, CCR3 and IL-17A is indicative for subtype 3; and, optionally,
(c3) the gene expression of at least 1 of the genes selected from IFN-γ, IL-5, IL-22, IL-23, GM-CSF and TGF-β is indicative for subtype 3;
(d) the patient is diagnosed with asthma subtype 4, if
(d1) the IgE level is equal to or higher than 300 IU/mL and the eosinophil level without steroids of higher than 700 cells/µl; and
(d2) the gene expression of any 5 or more of the genes selected from IFN-γ, IL-4, IL-5, IL-13, IL-33, GATA-3, CCR3 and IL-17A is indicative for subtype 4; and, optionally,
(d3) the gene expression of at least 1 of the genes selected from IL-10, IL-12, IL-2, IL-3, IL-5, IL-21, IL-25, CCL11, IL-22, IL-23, GM-CSF and TGF-β is indicative for subtype 4; or
(e) the patient is diagnosed with asthma subtype 5; if
(e1) the IgE level is equal to or more than 300 IU/mL and the eosinophil level without steroids is >300 and ≤700 cells/µl; and
(e2) the gene expression of any 6 or more, 7 or more or all 8 of the genes selected from IL-4, IL-5, IL-33, IL-37, IL-17A, IL-22, IL-23 and GM-CSF is indicative for subtype 5; and, optionally,
(e3) the gene expression of at least 1 of the genes selected from IL-6, IFN-γ, IL-21, IL-25 and TGF-β is indicative for subtype 5

In the method, the detection reagents for measuring the gene expression level, for example primers for the genes of interest, may be commercially available, for example from various manufacturers in a standardized quality (for example Affymetrix, Biorad, Life Technologies or Qiagen). Some prefabricated assay panels may also be commercially available. However, most prefabricated assay panels currently on the market are not intended for a specific combinatory use and evaluation, but are rather designed for basic research purposes and not for a specific diagnostic intention or method. Also, the use of the prefabricated assay panels currently available on the market for the diagnostic method may be suboptimal, because if only a plurality of isolated individual results is obtained, no systematic endotyping, and therefore no diagnosis of the asthma subtype and therapy recommendation, can be achieved. Therefore, in various embodiments, the assay panels described herein are used. This may also include the use of the specific multiwall plates described herein.

Evaluating the data includes a comparison of the determined gene expression levels of the at least six genes of interests with the gene expression levels of the same genes of interest in a healthy individual. The comparison may be performed the by means of a software. The comparison may include a classification of the differences between the gene expression level determined in the patient sample and the gene expression level of a healthy individual. For example, the determined gene expression level of each of the genes specifically selected for the patient may be classified in an increased gene expression level or decreased gene expression level based on predetermined thresholds or categories, as described above.

In some embodiments, the gene expression level of the at least six genes is measured by assaying for protein level and/or the mRNA level or cDNA level or by sequencing.

In one embodiment, the method of diagnosing the asthma subtype is a method at the transcriptome level. This represents a precise and unequivocal genomic means for diagnosis and therapy recommendation that indicates the activity state of the genome and goes beyond a "static" genotyping at the DNA level. The method is thus also a dynamic diagnostic means that can differentiate between different states of progression of the asthmatic endotypes. This also means that with the assay, the therapeutic effect or success of a treatment can be monitored, and the treatment can be changed or adjusted, based on the assay, in case of immunological adaptations or resistance development. In other words, an asthma subtype may be diagnosed using the methods described herein and/or the efficacy of an asthma treatment may be determined using the methods described herein. After the diagnosis of the asthma subtype and/or the determination of the efficacy of the asthma treatment, the dosage of the asthma treatment may be changed or the asthma treatment may be changed to a different asthma treatment based on the diagnosis and/or determination.

If the gene expression level is determined on mRNA level, the mRNA may be the mRNA transcript, a 5'- and/or 3'-truncated mRNA or spliced mRNA forms.

Where, in the methods detailed above, the binding part of the gene, e.g. the marker, is determined on mRNA level or cDNA level, the RNA or DNA level may be determined by PCR, gel electrophoresis and/or Northern Blot. In that case the detection reagent may be a nucleic acid molecule, such as an oligonucleotide. The oligonucleotide may be a nucleic acid probe that may be labeled to allow detection or may be an oligonucleotide primer that allows amplification of the target molecule.

The detection reagents for measuring the mRNA level or cDNA level of the gene may be a primer pair or a probe and the nucleic acid information of the genes is known in GeneBank and the like, a person skilled in the art can design a primer or a probe specifically amplifying a specific region of the gene based on the sequence. The detection reagent for measuring the mRNA level or the cDNA level of the gene may include a primer pair, a probe, or an antisense nucleotide that specifically binds to the gene.

In certain embodiment, the mRNA level or cDNA level is measured by PCR method, preferably RT-PCR (real time PCR), or microarray chip suitable to perform low(est) volume PCR, digital PCR or by sequencing. Detection may for example be achieved by using specific detection probes that are detectably labeled. Such techniques are widely known in the art and can be chosen by those skilled in art based on their general knowledge. According to one embodiment, a control gene is a housekeeping gene selected from 18 s and/or GAPDH.

If the gene expression level is determined on protein level, the protein may be the full length protein or a fragment thereof. The protein fragment may be a truncated protein, i.e. lack one or more amino acids at the N-terminus or C-terminus or both. This may be due to post-translational processing or due to the action of proteases present in the cell or the sample. The protein determined in the methods thus also include naturally occurring fragments, preferably immunogenic fragments. Also, the protein may be post-translationally modified, e.g., phosphorylated, hydroxylated, glycosylated, N-glycosylated, O-glycosylated, ubiquitinylated, acetylated, methylated, prenylated or sulphated.

In one embodiment, the protein expression level is determined by an immunoassay, ELISA, mass spectrometry, chromatography, Western Blot or gel electrophoresis. According to one embodiment, the immunoassay method comprises the steps of binding an antibody to protein expressed from a gene mentioned above in a patient sample mentioned above and determining if the protein level from the patient sample is elevated or decreased.

In some embodiments, the immunoassay may be, but is not limited to, an Enzyme-linked Immunosorbent Assay (ELISA), Western blot, agglutination test, biotin/avidin type assays, radioimmunoassays, immunoelectrophoresis and immunoprecipitation. The reactions generally include revealing labels such as fluorescent, chemiluminescent, radioactive, enzymatic labels or dye molecules, or other methods for detecting the formation of a complex between the antigen and the antibody or antibodies reacted therewith These and further immunoassays are well known in the art (David Wild (Ed.): The Immunoassay Handbook. $3^{rd}$ ed. Elsevier Science Publishing Company, Amsterdam 2005).

The aforementioned assays may involve separation of unbound protein in a liquid phase from a solid phase support to which antigen-antibody complexes are bound. Solid supports which can be used in the practice include substrates such as nitrocellulose (e. g., in membrane or microtiter well form), polypropylene (PP), polyethylene (PE), polycarbonate (PC), and/or other suitable polymers, polyvinylchloride (e. g., sheets or microtiter wells), polystyrene latex (e.g., beads or microtiter plates), polyvinylidine fluoride, diazotized paper, nylon membranes, activated beads, magnetically responsive beads, and the like.

More particularly, an ELISA method can be used, wherein the wells of a microtiter plate are coated with an antibody against the protein to be tested. A biological sample containing or suspected of containing the marker is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

In certain embodiments of the above detailed methods, if the determination is via mass spectrometry, the mass spectrometry may be selected from the group comprising MS measurements using EI, CI, ESI, APPI or APCI. More particularly also flow cytometry can be used.

The gene expression level determination on protein level employing chromatography may be selected from the group comprising liquid chromatography, HPLC, FPLC, Smart chromatography, gel chromatography, size exclusion chromatography, reverse phase chromatography and ion-exchange chromatography (Introduction to Modern Liquid Chromatography, Lloyd R. Snyder, 5 Wiley, 2009).

In various embodiments, if the gene expression level is detected via gel electrophoresis, the gel electrophoresis may be selected from the group, but not limited to agarose gel electrophoresis, sodium dodecyl sulfate poly acryl amide gel electrophoresis (SDS-PAGE), 2D-gel electrophoresis, native gel electrophoresis and quantitative preparative native continuous polyacrylamide gel electrophoresis (QPNC-PAGE).

Of course, in certain embodiments of the methods at least two determination methods may be coupled to each other in a subsequent manner. In a variant, a gel electrophoresis may be followed by a mass spectroscopic analysis. Alternatively, a gel electrophoresis may be followed by a Western Blot, a chromatography may be followed by a mass spectroscopic analysis, a chromatography may be followed by an immune assay, e.g. an ELISA.

In certain embodiments, the sample may be subjected to processing before the gene expression levels are determined. In one embodiment, the sample can, for example, be fractionated to enrich the nuclear matrix proteins (NMP).

NMPs may be enriched from any biological sample. In certain embodiments NMPs are enriched from cells, tissue or body fluid. The term "enriched" means that at least some NMP are present in higher concentrations in the enriched sample compared to the non-enriched sample. NMP preparations may be prepared by well-known methods in the art such as detergent and urea extraction (Getzenberg et al., Cancer Res, 51:6514-6520, 1991). An NMP preparation that is enriched in NMPs may additionally contain other proteins, i.e. proteins that are not part of the nuclear matrix.

For the detection of the proteins corresponding to the genes specific detection reagents, e.g. binding partners may be employed. In some embodiments, the specific binding partners are useful to detect the presence of a protein in a sample, wherein the detected part, e.g. the marker, is a protein or RNA. The marker and its binding partner represent a binding pair of molecules, which interact with each other through any of a variety of molecular forces including, for example, ionic, covalent, hydrophobic, van der Waals, and hydrogen bonding. Preferably, this binding is specific. "Specific binding" means that the members of a binding pair bind preferentially to each other, i.e. usually with a significant higher affinity than to non-specific binding partners. The binding affinity for specific binding partners is thus usually at least 10-fold, preferably at least 100-fold higher than that for non-specific binding partners.

Exemplary binding partners are selected from the group consisting of antibodies, antibody fragments and variants, molecules with antibody-like properties, such as lipocalin muteins or Spiegelmers or aptamers. Antibody fragments and variants include Fv fragments, linear single chain antibodies and the like all of which are known to those skilled in the art.

When in relation to the marker genes the term "fragment" is used herein, it is meant that the respective gene expression level may be determined by assaying for a certain nucleotide stretch of the respective gene, i.e. a gene fragment, or a fragment of an expression product of said gene, such as RNA or protein, that still allows determination of the gene expression level in that it is specific for the gene.

In various embodiments, evaluating the data may comprise evaluating the determined gene expression level of the at least six genes of interest in the light of, e.g. taking into consideration, further information about the patient to be diagnosed. For example, the further information may encompass, but are not limited to, the phenotype of the asthma condition, the intake of medication and/or the results of measurement of systemic biomarkers. The phenotype may include, but is not limited thereto, bronchial asthma, an atopic asthma, a non-atopic asthma, an exercise induced asthma, an aspirin-sensitive asthma, a psychogenic asthma, a common asthma, an eosinophilic-neutrophilic asthma, mixed asthma, occupational asthma, cough-variant asthma, coexistent asthma, asthma COPD (chronic obtrusive pulmonary diseases), asthma COPD overlap syndrome (ACOS) or today asthma-chronic obstructive pulmonary disease overlap (ACO) or alveolar asthma. The intake of medication may encompass the intake of drugs that may affect the gene expression levels in a patient, for example the intake of steroids. Steroids may modify the parameters relevant for inflammation substantially, so that the reference values to be considered when evaluating the data should be adapted. Systemic biomarkers typically are non-genetic biomarkers and are typically measured in samples obtained by invasive or noninvasive procedures, for example, but not limited to, collection of blood or blood components, like serum or plasma, or sputum. The systemic biomarkers may be selected, for example, from serum CEA levels, serum IgE full levels, serum periostin levels, peripheral blood eosinophil counts, eosinophil percentages in bronchoalveolar lavage fluid (BAL), and neutrophil levels or the nitric oxides in the exhaled breath (FeNO: fractional exhaled nitric oxide). In various embodiments, this clinical diagnosis step includes determination of IgE, eosinophil and neutrophil levels in peripheral blood, as described above. The eosinophilic levels may be useful for the diagnosis of "eosinophilic asthma" as indication for a therapy with Mepolizumab. The IgE full levels may be useful for the diagnosis of allergic asthma and for a therapy with the medication Omalizumab at an appropriate dosage.

The evaluation is, in various embodiments, performed by a special software developed for the method. Said software may be a customized standard software that allows a recommendation of a therapy based on a systemic combinatory and weighed evaluation of the specific detection reagents used in the assay for measuring the gene expression level of specific genes. How these can be evaluated and, if desired, weighted has already been described above. In some embodiments, the software is based on combinatory algorithms and determines the asthma type of the patient from the determined gene expression levels of the genes of interest, and optionally, predetermined clinical and/or chemical parameters of asthma subtypes existing in asthma patients. The software correlates the determined gene expression levels of the genes of interest in a combinatorial weighted relationship with each other, e.g. performs calculation to obtain a combinatorial cytokine/receptor profile. By means of the software and based on the calculated relationships between the determined gene expression levels of the genes of interest, the gene expression profile or pattern specific to the patient is obtained ("gene expression profile"). Optionally, the software further establishes the relationship between the calculated relationships between the determined gene expression levels of the genes of interest and/or defined clinical and laboratory chemical parameters. It results then a data matrix (table of factor values), which, based on the predetermined thresholds or categories, results in an endotyping of the asthma condition of the patient to be diagnosed as well as a recommendation for the most promising antibody therapy ("endotypical profiling").

In certain embodiments, the asthma subtype is a severe asthma type, preferably an asthma subtype selected from the group consisting of a severe allergic asthma, a severe non-allergic asthma, eosinophilic allergic asthma, non-eosinophilic allergic asthma, non-allergic asthma, Th-1-cell characterized asthma, Th-2-cell characterized asthma or Th-17-cell characterized asthma. The genes are thus selected from genes which are specific for asthma subtypes for the differentiation of gene expression profile in patients suffering from, for example, a severe allergic asthma, a severe non-allergic asthma, eosinophilic allergic asthma, non-eosinophilic allergic asthma, non-allergic asthma, Th-1-cell characterized asthma, Th-2-cell characterized asthma, Th-17-cell characterized asthma, but not limited to these subtypes.

In some embodiments, the sample is a biological sample, preferably body fluid, cell or tissue sample. The body fluids comprise but are not limited to blood, serum, plasma and sputum, with blood being particularly preferred. The tissue sample may be lung tissue and the cell sample may comprise cells from lung tissue.

In various embodiment, the patient to be diagnosed is a mammal, preferably a human. The patient may be suspected of having or at risk for having asthma or be diagnosed with asthma.

In a further aspect, a kit may be used in the method, wherein the kit is a combinatory asthma endotyping kit comprising detection reagents for measuring the gene expression level of at least six genes selected from the group consisting of detection reagents for measuring the gene expression level of at least six genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more selected from the group selected from IL-8, IL-10, IL-12, IL-27, TNF-α, CD94, IL-3, IL-9, IL-31, IL-35, CCL11 and TGF-β or fragments thereof, optionally further including an instruction manual for measuring the gene expression level of the genes comprised in the combinatory asthma endotyping kit and, optionally, a software, wherein the software is configured to evaluate data measured and determine the asthma subtype of the patient.

In some embodiments, the kit may further comprise one or more other component compositions, solutions (such as buffers and the like) or devices suitable to carry out the method.

In addition, a combinatory asthma endotyping panel may include detection reagents for measuring the gene expression level of at least six genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23 and GM-CSF or fragments thereof and optionally one or more selected from the group selected from IL-8, IL-10, IL-12, IL-27, TNF-α, CD94, IL-3, IL-9, IL-31, IL-35, CCL11 and TGF-β or fragments thereof for use in a method. The combinatory asthma endotyping panel differs significantly from the assay panels available commercially that are essentially designed as PCR arrays of gene expression panels for the basic research and thus do not comprise a focused combination of genes of specific cytokines. Furthermore, such assay panels are generally not used or permitted for diagnostic purposes.

In some embodiments, the combinatory asthma endotyping panel comprises a microtiter plate, for example a PCR-microtiter plate, which is prepared with specifically selected primers for the cytokines of interest in a specific combination. Typically, the primers are immobilized in the wells of such a plate and, subsequently, the PCR-microtiter plate may be sealed. Such a sealed combinatory asthma endotyping panel microtiter plate may have a shelf life of 6 months at a temperature of −20° C.

The microtiter plate may be modified for the handling simplification in the clinical laboratory routine or to prevent pipetting errors.

Figures 1, 2:
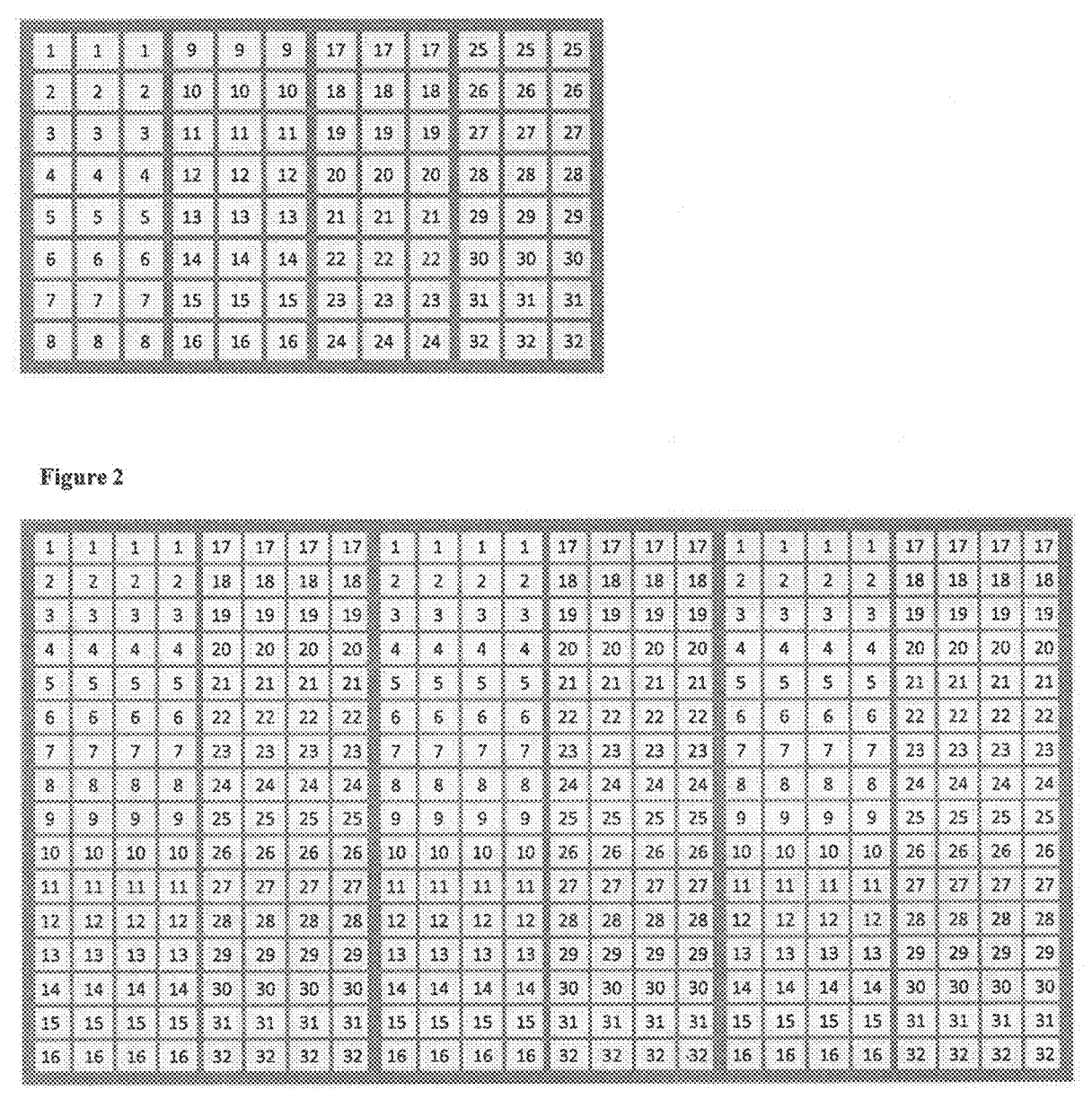

FIG. 1 shows a schematic drawing of a well layout of a 96 PCR well microtiter plate for one patient, wherein the gene expression level of 30 genes+2 housekeeping genes can be determined. The 96 PCR well microtiter plate comprises a standardized combination of 30+2 primers, wherein each primer sample has three technical replicates.

FIG. 2 shows a schematic drawing of a well layout of a 384 PCR well microplate for up to three patients, wherein the gene expression level of 30 genes+2 housekeeping genes can be determined. The 384 PCR well microtiter plate comprises a standardized combination of 30+2 primers, wherein each primer sample has four technical replicates.

Figures 3, 4:
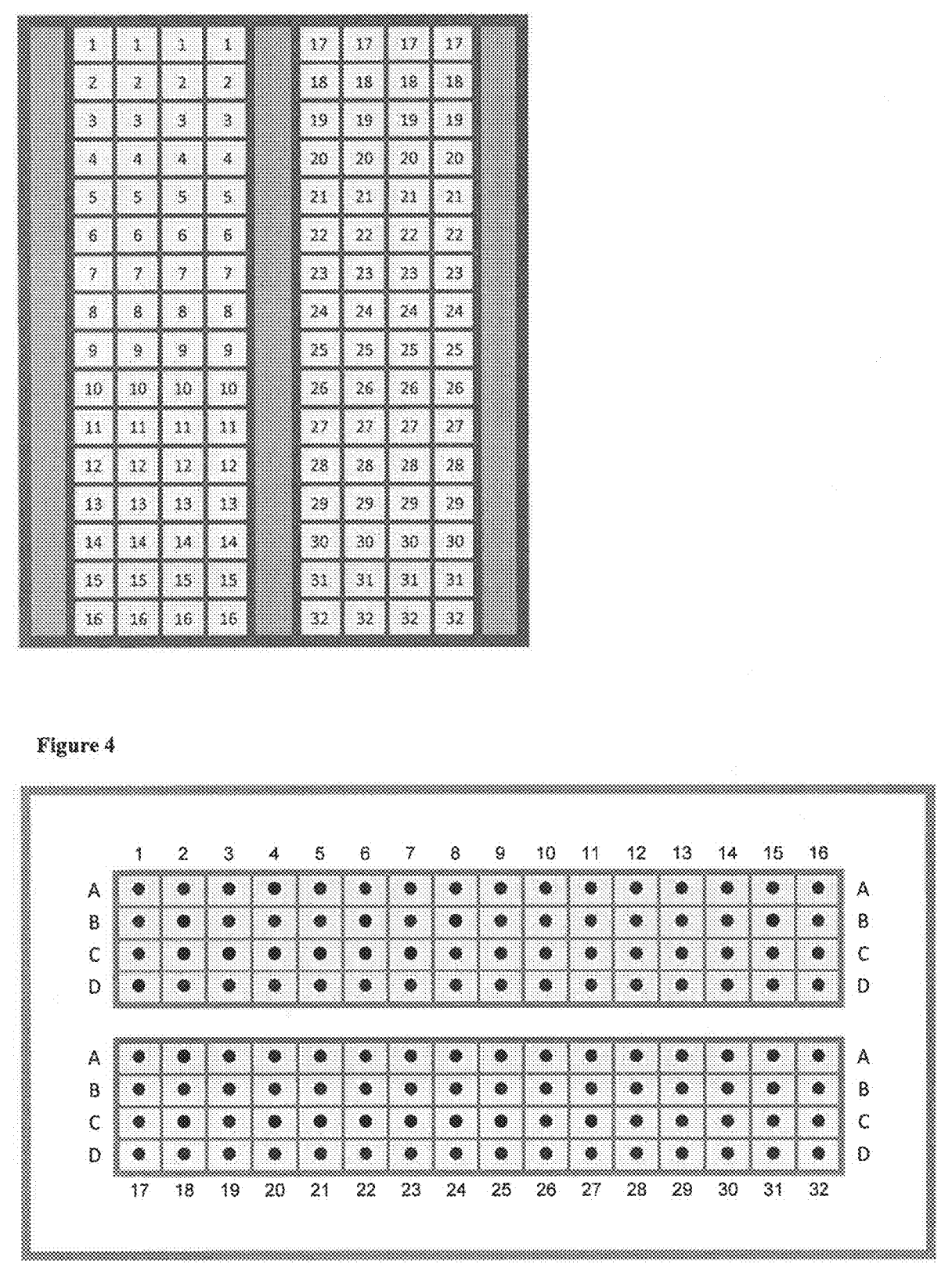

FIG. 3 shows a schematic drawing of a well layout of a dedicated PCR well microplate for one patient, wherein the dedicated PCR well microplate is compatible with the 384 SBS format, wherein the gene expression level of 30 genes+2 housekeeping genes can be determined. The dedicated PCR well microplate comprises a standardized combination of 30+2 primers, wherein each primer sample has four technical replicates.

The plates shown in the Figures also represent one aspect.

By means of a specifically manufactured PCR-microtiter plate in the 384 SBS format, as shown in FIG. 3, the combinatory asthma endotyping panel leads to material and costs savings in comparison to standard 96 or 384 microtiter plates and simplifies especially the manual pipetting of the required substances. The costs of the combinatory asthma endotyping panel are significantly below the usual prices for manufactured assay panels in microtiter plates available on the market and make the combinatory asthma endotyping panel attractive for the clinical routine diagnosis and the reimbursement from health insurances.

The combinatory asthma endotyping panel is compatible with standard acquisition systems of laboratory devices for microtiter plates, for example PCR-microtiter plates in 98 or 384 SBS format. For example, two the microtiter plates as shown in FIG. 3 vertically mounted next to each other fit into the standard 384 acquisition systems of PCR devices.

In a further embodiment, the combinatory asthma endotyping panel may be a ready-to-use Lab-on-a-Chip. FIG. 4 shows a basic schematic layout of a dedicated lab-on-chip device for one patient, wherein the gene expression level of 30 genes+2 housekeeping genes can be determined. The chip comprises a standardized combination of 30+2 primers, wherein each primer sample has four technical replicates. The physical design of the Lab-on-Chip according to this embodiment allows PCR analyses in the sub-microliter scale.

Another aspect relates to a method for monitoring the therapeutic effect of an asthma treatment in a patient, the method comprising performing the method of diagnosing an asthma subtype in a patient before administering to the patient the asthma treatment, performing the method of diagnosing an asthma subtype in a patient at least once at a predetermined time after administering to the patient the asthma treatment, and determining the efficacy of said therapeutic treatment based on the evolution in gene expression levels of the genes of interest before administering the asthma treatment and after administering the asthma treatment to the patient. Based on the efficacy determination, the treatment can be changed or adjusted in case of immunological adaptations or resistance development. In other words, an asthma subtype may be diagnosed using the methods described herein and/or the efficacy of an asthma treatment may be determined using the methods described herein. After the diagnosis of the asthma subtype and/or the determination of the efficacy of the asthma treatment, the dosage of the asthma treatment may be changed or the asthma treatment may be changed to a different asthma treatment based on the efficacy determination.

In one embodiment, the asthma treatment comprises an antibody treatment, preferably an anti-IgE antibody treatment, an anti-IL-5 antibody treatment, an anti-IL-17 antibody treatment and/or an anti-IL-4 antibody treatment, depending on the respective subtype determined in the first step. The asthma immunotherapy with antibodies may be combined with steroid therapy/administration.

All embodiments disclosed herein for the methods are similarly applicable to all other aspects, such as, for example, the kits, the uses, the plates and vice versa.

EXAMPLES

Example 1: Method

Patient A was diagnosed with severe allergic asthma. She/He had not taken steroids systemically for at least 4 weeks. The initial IgE concentration was 300 IU/ml. The eosinophilic count was 1000 cells/µl in the blood stream. Both parameters had been obtained by routine diagnostic methods.

By venous puncture 2.5 ml of whole blood were collected in a PAXgeneR Blood RNA Tube (PreAnalytiX GmbH, Schwitzerland). The blood tube was kept at room temperature for two hours according to the manufacturer's instructions to safeguard the complete lyses of blood cells.

The RNA was isolated by using the PAXgene® Blood RNA Kit (v2 PreAnalytiX, GmbH, Schweiz) according to the instructions of the manufacturer. RNA was quantified by using the NanoDrop® ND1000 SN Spectrophotometer (PEQLAB Biotechnologie GmbH, Germany).

183.8 ng/µl total RNA were isolated. [The 260/280 ratio was 2.1 indicating "pure" RNA.]

To synthesize cDNA from total RNA, the High-Capacity cDNA Reverse Transcription Kit from Applied Biosystems (cat. no. 4368814) was used. 500 ng of total RNA were used per 20 µl reaction volume. cDNA was prepared according to the manufacturer's instruction on the Eppendorf Thermo-Cycler with a temperature cycle as recommended by the manufacturer (25° C.: 10 min; 37° C.: 120 min and 85° C.: 5 min). Samples were immediately placed on ice.

The qRT-PCR was carried out using predesigned TaqMan® primers (FAM™ dye-labeled; Table 1; Life Technologies GmbH, Darmstadt, Germany). The TaqMan gene expression arrays were performed in 96-wellplates on a TaqMan Thermal Cycler 7300 System in a reaction volume of 20 µl with the ready to use TaqMan gene expression master mix (Applied Biosystems, Thermo Fisher Scientific, cat. No. 4369016) in quadruplicates for each primer. qRT-PCR conditions were as follows: 50° C.: 2 min (1×); 95° C.: 10 min (1×); 95° C.: 15 sec (40×); 60° C.: 1 min (40×).

Calculation of results: the mean of the 18sRNA for each replicate was subtracted from the corresponding gene value to normalize the data (ΔCt). Results were calculated as $2^{-\Delta\Delta Ct}$.

The obtained data express the fold changes of gene expression compared to the respected mean of the pre-defined control group.

TABLE 1

List of Genes and TAQ-Man Primers (as available from Thermo Fisher Scientific)

| Gene Name | Gene Symbol | Gene ID | TAQ-Man Primer ID |
|---|---|---|---|
| Interleukin 1β | IL-1β | 3553 | Hs01555410_m1 |
| Interleukin 2 | IL-2 | 3558 | Hs00174114_m1 |
| Interleukin 4 | IL-4 | 3565 | Hs00174122_m1 |
| Interleukin 5 | IL-5 | 3567 | Hs01548712_g1 |
| Interleukin 6 | IL-6 | 3569 | Hs00985639_m1 |
| Interleukin 8 | IL-8 | 3576 | Hs00174103_m1 |
| Interleukin 10 | IL-10 | 3586 | Hs00961622_m2 |
| Interleukin 13 | IL-13 | 3596 | Hs00174379_m1 |
| Interleukin 17A | IL-17A | 3605 | Hs00174383_m1 |
| Interleukin 21 | IL-21 | 59067 | Hs01574154_m1 |
| Interleukin 33 | IL-33 | 90865 | Hs00369211_m1 |
| C_Cmotif chemokine receptor 3 | CCR3 | 1232 | Hs04931117_m1 |
| Interferon γ | IFN-γ | 3458 | Hs00989291_m1 |
| Thymic stromal lymphoietin | TSLP | 85480 | Hs00263639_m1 |
| Tumor necrosis factor α | TNF-α | 7124 | Hs01113624_g1 |
| Eukaryotic 18S rRNA Endogenous Control (FAM ™/MGB) | RNA18S5 | — | Hs03928990_g1 |

The following results were obtained (core markers shown in bold):

| Gene | Expression level (fold change relative to mean of control group) |
|---|---|
| Interleukin 1β | 12.3 |
| Interleukin 2 | 3.3 |
| Interleukin 4 | 40.1 |
| Interleukin 5 | 1002 |
| Interleukin 6 | 1.8 |
| Interleukin 8 | 0.88 |
| Interleukin 10 | 0.61 |
| Interleukin 13 | 15.3 |
| Interleukin 17A | 0.025 |
| Interleukin 21 | 1.2 |
| Interleukin 33 | 49.5 |
| C_Cmotif chemokine receptor 3 | 151 |
| Interferon γ | 5.2 |
| Thymic stromal lymphopoietin | 2 |
| Tumor necrosis factor α | 1.9 |

Conclusion: Classification as Subtype SP4
Recommendation: Anti-IL-5 Antibody.

Various publications and/or references have been cited herein, the content of which are incorporated herein by reference.

While particular embodiments have been illustrated and described, it would be obvious to those skilled in the art that various other changes and modifications can be made without departing from the scope of the invention. It is therefore intended to cover in the appended claims all such changes and modifications that are within the scope of this invention.

The invention claimed is:

1. A kit, wherein the kit is a combinatory asthma endotyping kit and comprises:
detection reagents for measuring a gene expression level of at least six genes selected from the group consisting of IL-1β, IL-6, IFN-γ, IL-2, IL-4, IL-5, IL-13, IL-21, IL-25, IL-33, IL-37, TSLP, GATA-3, CCR3, IL-17A, IL-22, IL-23, GM-CSF, fragments thereof, and combinations thereof, and optionally one or more selected from the group consisting of IL-8, IL-10, IL-12, IL-27, TNF-α, CD94, IL-3, IL-9, IL-31, IL-35, CCL11, TGF-β, fragments thereof, and combinations thereof to obtain the gene expression profile of the patient, wherein the detection reagents include a labeled detection probe adapted to allow detection of an expressed gene in the groups by detecting the labeled detection probe during or after an amplification reaction;
optionally an instruction manual for measuring the gene expression levels of genes comprised in the kit; and
a software, wherein the software is configured to be executed by a processor to determine an asthma subtype of the patient by comparing the gene expression profile of the patient with reference gene expression profiles of one or more of Tables 4-8, wherein the comparing is performed based on weighed threshold gene expression values indicated in Table 2, wherein optionally the list of core markers of Table 3 may be used for ruling out asthma subtypes.

2. A combinatory asthma endotyping system comprising detection reagents for measuring the gene expression level of at least six genes selected from the group consisting of IL-1, IL-6, IFN-γ IL-2, IL-4, IL-5, IL-13, IL-21, IL-25, IL-33, IL-37, TSLP, GATA-3, CCR3, IL-17A, IL-22, IL-23, GM-CSF, fragments thereof, and combinations thereof, and optionally one or more selected from the group selected from IL-8, IL-10, IL-12, IL-27, TNF-α, CD94, IL-3, IL-9, IL-31, IL-35, CCL11, TGF-β fragments thereof, and combinations thereof to obtain the gene expression profile of the patient, wherein the detection reagents include a labeled detection probe adapted to allow detection of an expressed gene in the groups by detecting the labeled detection probe during or after an amplification reaction; and
a software, wherein the software is configured to be executed by a processor to determine an asthma subtype of the patient by comparing the gene expression profile of the patient with reference gene expression profiles of one or more of Tables 4-8 wherein the comparing is performed based on weighed threshold gene expression values indicated in Table 2, wherein optionally the list of core markers of Table 3 may be used for ruling out asthma subtypes.

* * * * *